(12) United States Patent
Bowser et al.

(10) Patent No.: US 7,858,071 B2
(45) Date of Patent: *Dec. 28, 2010

(54) BIOMARKERS FOR AMYOTROPHIC LATERAL SCLEROSIS

(75) Inventors: Robert P. Bowser, Cranberry Township, PA (US); Srikanth Ranganathan, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1220 days.

This patent is subject to a terminal disclaimer.

(21) Appl. No.: 10/972,732

(22) Filed: Oct. 25, 2004

(65) Prior Publication Data

US 2005/0148026 A1  Jul. 7, 2005

Related U.S. Application Data

(60) Provisional application No. 60/513,930, filed on Oct. 23, 2003.

(51) Int. Cl.
 *A61K 49/00* (2006.01)
 *C40B 30/10* (2006.01)
 *G01N 33/00* (2006.01)
 *G01N 33/48* (2006.01)

(52) U.S. Cl. .................. 424/9.1; 435/7.95; 702/19; 506/6

(58) Field of Classification Search .................. 702/22; 436/86, 94, 173; 435/7.1
 See application file for complete search history.

(56) References Cited

U.S. PATENT DOCUMENTS

| | | | |
|---|---|---|---|
| 5,719,060 A | 2/1998 | Hutches et al. | |
| 5,792,664 A | 8/1998 | Chait et al. | |
| 6,294,790 B1 | 9/2001 | Weinberger | |
| 6,618,138 B2 | 9/2003 | Khoury | |
| 6,675,104 B2 | 1/2004 | Paulse et al. | |
| 6,776,984 B1 | 8/2004 | Schwartz | |
| 7,005,255 B2 | 2/2006 | Kaddurah-Daouk | |
| 7,572,596 B2 | 8/2009 | Bowser | |
| 2002/0138208 A1* | 9/2002 | Paulse et al. ................. | 702/22 |
| 2003/0013120 A1* | 1/2003 | Patz et al. .................... | 435/7.1 |
| 2004/0033530 A1 | 2/2004 | Awrey et al. | |
| 2005/0148026 A1 | 7/2005 | Bowser et al. | |
| 2006/0121619 A1 | 6/2006 | Bowser | |

FOREIGN PATENT DOCUMENTS

| | | |
|---|---|---|
| WO | WO 93/24834 | 12/1993 |
| WO | WO 93/24834 A1 | 12/1993 |
| WO | WO 98/59360 | 12/1998 |
| WO | WO 98/59360 A1 | 12/1998 |
| WO | WO 03/006973 | 1/2003 |
| WO | WO 2006/071469 | 7/2006 |

OTHER PUBLICATIONS

Lomen-Hoerth C., "Amyotrophic lateral sclerosis from bench to bedside", Semin Neurol. Apr. 2008;28(2):Abstract.*
Davidsson et al., Journal of Neural Transmission, 104:711-720, 1997.*
Puchades et al., Rapid Commun in Mass Spectrom., 13:2450-2455, 1999.*
Ruetschi et al., Experimental Neurology, 196:273-281, 2005.*
Yang et al., Cell Mol Neurbiol., 28:737-744, 2008.*
Planté-Bordeneuve et al., Curr Opin Neurol., 13(5):569-573, 2000.*
Cudkowicz et al., "Measures and Markers in Amyotrophic Lateral Sclerosis," *NeuroRx: The Journal of the American Society for Experimental Neuro Therapeutics*, 1(2): 273-283 (Apr. 2004).
Abrahamson et al., *FEBS Letters*, 216(2), 229-233 (1987).
Borchelt et al., *Proceedings of the National Academy of Sciences of the United States of America*, 91(17), 8292-8296 (1994).
Bowser et al., *The FASEB Journal*, 17(4), A658 (2003).
Cleveland et al., *Nature Reviews Neuroscience*, 2, 806-819 (2001).
Desnuelle et al., *Amyotrophic Lateral Sclerosis and Other Motor Neuron Disorders*, 2(1), 9-18 (2001).
Feigenbaum et al., *Artificial Intelligence*, 59, 233-240 (1993).
Groeneveld et al., *Annals of Neurology*, 53(4), 437-445 (2003).
Jellinger, *Movement Disorders*, 18(Supplement 6), S2-S12 (2003).
Kim et al., *Journal of Neuropathology & Experimental Neurology*, 62(1), 88-103 (2003).
Lee et al., *Environmental Health Perspectives*, 104(Supplement 5), 1059-1063 (1996).
Levy et al., *The Journal of Experimental Medicine*, 169(5), 1771-1778 (1989).
Martens, *FEBS Letters*, 234(1), 160-164 (1988).
Menzies et al., *Brain A Journal of Neurology*, 125(7), 1522-1533 (2002).
Miller et al., *Amyotrophic Lateral Sclerosis and Other Motor Neuron Disorders*, 4(3), 191-206 (2003).
Mita et al., *Biochemical and Biophysical Research Communications*, 124(2), 558-564 (1984).
Nagai et al., *The Journal of Neuroscience*, 21(23), 9246-9254 (2001).
Paulson, *The American Journal of Human Genetics*, 64(2), 339-345 (1999).
Ranganathan et al., *Amyotrophic Lateral Sclerosis and Other Motor Neuron Disorders*, 3(Supplement 2), 57 (2002).
Ranganathan et al., *The American Journal of Pathology*, 162(3), 823-835 (2003).
Rosen et al., *Nature*, 362(6415), 59-62 (1993).
Rosen et al., *Human Molecular Genetics*, 3(6), 981-987 (1994).

(Continued)

*Primary Examiner*—Elizabeth C. Kemmerer
*Assistant Examiner*—Stacey MacFarlane
(74) *Attorney, Agent, or Firm*—Pabst Patent Group LLP

(57) ABSTRACT

The invention provides a method for diagnosing amyotrophic lateral sclerosis (ALS) in a subject, a method for assessing the effectiveness of a drug in treating ALS, and a method for determining the site of onset of ALS in a subject. Each method comprises (a) obtaining a sample from the subject, (b) analyzing the proteins in the sample by mass spectroscopy, and (c) determining a mass spectral profile for the sample. In some embodiments, the method comprises comparing the mass spectral profile of the sample to the mass spectral profile of a positive or a negative standard.

3 Claims, 2 Drawing Sheets

OTHER PUBLICATIONS

Shaw et al., *Amyotrophic Lateral Sclerosis and Other Motor Neuron Disorders*, 1(Supplement 2), S61-S67 (2000).
Smith et al., *Annals of Neurology*, 44(4), 696-699 (1998).
Spreux-Varoquaux et al., *Journal of Neurological Sciences*, 193(2), 73-78 (2002).
Subramaniam et al., *Nature Neuroscience*, 5(4), 301-307 (2002).
Tsuzuki et al., *The Journal of Biological Chemistry*, 260(22), 12224-12227 (1985).
U.S. Appl. No. 60/632,380, filed Dec. 2, 2004, Bowser.
U.S. Appl. No. 60/632,450, filed Dec. 2, 2004, Bowser.
Bowser, et al, "Protein Profiling of amyotrophic lateral sclerosis patients by mass spectrometry" *Federation of American Societies for Exp. Bio. Annu Meeting Abstracts* 17:4-5(2003).
Kikuchi, et al. "Immunohistochemical analysis of spinal cord lesions in amyotrophic lateral sclerosis using microtubule-associated protein 2 (MAP2) antibodies" *Acta Neuropathologica* 97(1)13-21(1999).
Malaspina, et al. "Differential expression of 14 genes in amyotrophic lateral sclerosis spinal cord detected using gridded cDNA arrays" *J. Neurochemistry* 77(1)132-145(2001).
Ono, et al. "Increased Cystatin C immunoreactivity in the skin in amyotrophic lateral sclerosis" *Acta Neurologica Scandinavica* 102(1)47-52 (2000).
Pompl, et al. "Pharmacotherapeutic Biomarker Discovery in a Mouse Model of amyotrophic Lateral Sclerosis" *Abstract Viewer/ intinerary planner, Society of Nueroscience* 2002:1(2002).
Ranganathan, et al. "Proteomic profiling of cerebrospinal fluid identifies biomarkers for amyotrophic lateral sclerosis" *J. Neurochemistry* 95(5):1461-1471(2005).
Ranganthan, et al. "Altered expression of cell cycle regulators in amyotrophic lateral sclerosis" *Society for Nueroscience Abstracts* 27(2):1649 (2001).
Shimizu, et al. "Detection and identification of protein variants and adducts in blood and tissues: an application of soft ionization mass spectrometry to clinical diagnosis" *J. Chrom. B* 776(1):15-30(2002).
Abrahamson et al., "Structure and Expression of the Human Cystatin C Gene," *TheBiochemical Journal*, 268(2):287-94 (1990).
Abrahamson, et al., "The human cystatin C gene (CST3), mutated in hereditary cystatin C amyloid angiopathy, is located on chromosome 20," *Hum. Genet.*, 82(3):223-6 (1989).
Aizawa, et al., "Basophilic cytoplasmic inclusions in a case of sporadic juvenile amyotrophic lateral sclerosis," *J. Neurol. Sci.* 176:109-13 (2000).
Asgeirsson, et al., "Hereditary cystatin C amyloid angiopathy: monitoring the presence of the Leu-68—>Gln cystatin C variant in cerebrospinal fluids and monocyte cultures by MS," *Biochem. J.*, 329 (Pt 3):497-503 (1998).
Berg et al., "Exploring Proteins," *Biochemistry*, 1-6, W. H. Freeman and Company: New York, 2002. Relevant chapter portions accessed at URL: ncbi.nlm.nih.gov/books/bv.fcgi?highlight=immunological%20techniques&rid=s-tryer.section.506#507.
Carrette, et al., "A panel of cerebrospinal fluid potential biomarkers for the diagnosis of Alzheimer's disease," *Proteomics*, 3(8):1486-94 (2003).
Deng, et al., "Elevation of cystatin C in susceptible neurons in Alzheimer's disease," *Am. J. Pathol.*, 159(3):1061-8 (2001).
Kato, et al., "A neurosphere-derived factor, cystatin C, supports differentiation of ES cells into neural stem cells," *Proc. Natl. Acad. Sci. U.S.A.*, 103(15):6019-24 (2006).
Lofberg, et al., "Immunohistochemical characterization of the amyloid deposits and quantitation of pertinent cerebrospinal fluid proteins in hereditary cerebral hemorrhage with amyloidosis," *Stroke*, 18(2):431-40 (1987).
Nagai, et al., "Cystatin C and cathepsin B in CSF from patients with inflammatory neurologic diseases," *Neurology*, 55(12):1828-32 (2000).
Okamoto, et al., "Bunina bodies in amyotrophic lateral sclerosis immunostained with rabbit anti-cystatin C serum," *Neurosci. Lett.*, 162(1-2):125-8 (1993).

Sanchez, et al., "Cystatin C as a potential cerebrospinal fluid marker for the diagnosis of Creutzfeldt-Jakob disease," *Proteomics*, 4(8):2229-33 (2004).
Wada, et al., "Bunina bodies in amyotrophic lateral sclerosis on Guam: a histochemical, immunohistochemical and ultrastructural investigation," *Acta Neuropathol.*, 98(2):150-6 (1999).
Xu, et al., "Cystatin C prevents degeneration of rat nigral dopaminergic neurons: in vitro and in vivo studies," *Neurobiol. Dis.*, 1 8( 1): 152-65 (2005).
Yakota, et al., "Amyotrophic lateral sclerosis with dementia: an autopsy case showing many Bunina bodies, tau-positive neuronal and astrocytic plaque-like pathologies, and pallido-nigral degeneration,"*Acta Neuropathol.*, 112(5):633-45 (2006).
Benson et al., "Identification of Carriers of a Variant Plasma Prealbumin (Transthyretin) Associated With Familial Amyloidotic Polyneuropathy Type I," *The Journal of Clinical Investigation*, 75: 71-75 (1985).
Bergen et al. "Identification of Transthyretin Variants by Sequential Proteomic and Genomic Analysis," *Clinical Chemistry*, 50(9): 1544-1552 (2004).
Bernstein et al., "Transthyretin: Its Response to Malnutrition and Stress Injury" *Clin Chem Lab Med*, 40(12): 1344-1348 (2002).
Chaudhuri et al., "The Neuroendocrine Protein 7B2 Acts as a Molecular Chaperone in the In Vitro Folding of Human Insulin-Like Growth Factor-1 Secreted From Yeast," *Biochemical and Biophysical Research Communications*, 211(2): 417-425 (Jun. 15, 1995).
Connors et al., "Tabulation of Human Transthyretin (TTR) Variants, 2003," *Amyloid*, 10(3): 160-184 (Sep. 2003).
Corcoran et al., "Absence of Retinoids Can Induce Motoneuron Disease in the Adult Rat and a Retinoid Defect is Present in Motoneuron Disease Patients," *Journal of Cell Science*, 115(24): 4735-4741 (Dec. 15, 2002).
Fernandez et al., "Thyroid Hormone Administration Enhances Remyelination in Chronic Demyelinating Inflammatory Disease," *Proc. Natl. Acad. Sci. USA*, 101(46): 16363-16368 (Nov. 16, 2004).
Goodall et al., "Association of the H63D Polymorphism in the Hemochromatosis Gene with Sporadic ALS," *Neurology*, 65(6): 934-937, (2005).
Gurney et al., "Motor Neuron Degeneration in Mice That Express a Human Cu, Zn Superoxide Dismutase Mutation," *Science*, 264: 1772-1775 (Jun. 17, 1994).
Gurney et al., "Benefit of Vitamin E, Riluzole, and Gabapentin in a Transgenic Model of Familial Amyotrophic Lateral Sclerosis," *Annals of Neurology*, 39(2): 147-157 (Feb. 1996).
U.S. Appl. No. 11/294,161, filed Dec. 2, 2005, Bowser.
U.S. Appl. No. 11/294,326, filed Dec. 2, 2005, Bowser.
Hillbnkamp et al. "Matrix Assisted UV-Laser Desorption/Ionization: A New Approach to Mass Spectrometry of Large Biomolecules," *Biological Mass Spectrometry*, (Burlingame and McCloskey, eds) Elsevier, Amsterdam, 49-60 (1990).
Kamel et al., "Lead Exposure and Amyotrophic Lateral Sclerosis," *Epidemiology*, 13(3): 311-319 (May 2002).
Kriz et al., "Efficient Three-Drug Cocktail for Disease Induced by Mutant Superoxide Dismutase," *Annals of Neurology*, 53(4): 429-436 (Apr. 2003).
Lin et al., "Large-scale protein identification using mass spectrometry," *Biochimica et Biophysica Acta*, 1646(1-2): 1-10 (2003).
Martens et al. "The Novel Pituitary Polypeptide 7B2 is a Highly-Conserved Protein Coexpressed With Proopiomelanocortin," *European Journal of Biochemistry*, 181(1): 75-79 (Apr. 1989).
Mbikay et al., "Neuroendocrine Secretory Protein 7B2: Structure, Expression and Functions," *Biochemical Journal*, 357(2): 329-342 (Jul. 15, 2001).
Mey et al., "Retinoic Acid Signaling in the Nervous System of Adult Vertebrates," *The Neuroscientist*, 10(5): 409-421 (2004).
Ong et al., "An Evaluation of the Use of Two-Dimensional Gel Electrophoresis in Proteomics," *Biomolecular Engineering*, 18(5): 195-205 (Nov. 2001).
Palha, "Transthyretin as a Thyroid Hormone Carrier: Function Revisited," *Clinical Chemistry and Laboratory Medicine*, 40(12): 1292-1300 (Dec. 2002).

Paquet et al., "The Neuroendocrine Precursor 7B2 Is a Sulfated Protein Proteolytically Processed by a Ubiquitous Furin-Like Convertase," *The Journal of Biological Chemistry*, 269(30): 19279-19285 (Jul. 29, 1994).

Polpl et al., "Pharmacotherapeutic Biomarker Discovery in a Mouse Model of Amyotrophic Lateral Sclerosis," *Society for Neuroscience Abstract Viewer and Itinerary Planner*, 2002: 1 (Nov. 2002).

Ranganathan et al., "Protein Profiling of Amyotrophic Lateral Sclerosis Patients by Mass Spectrometry," *FASEB Journal*, 17(4-5): 1 (Mar. 2003).

Ranganathan et al. "Proteomic Profiling of Cerebrospinal Fluid Identifies Biomarkers for Amyotrophic Lateral Sclerosis," *Journal of Neurochemistry*, 95(5): 1461-1471 (Dec. 2005).

Rothstein et al., "β-Lactam antibiotics offer neuroprotection by increasing glutamate transporter expression," *Nature*, 433(7021): 73-77 (Jan. 6, 2005).

Sousa et al., "Deposition of Transthyretin in Early Stages of Familial Amyloidotic Polyneuropathy," *American Journal of Pathology*, 159(6): 1993-2000 (Dec. 2001).

Sousa et al., "Evidence for Early Cytotoxic Aggregates in Transgenic Mice for Human Transthyretin Leu55Pro," *American Journal of Pathology*, 161(5): 1935-1948 (Nov. 2002).

Sousa et al., "Neurodegeneration in Familial Amyloid Polyneuropathy: From Pathology to Molecular Signaling," *Progress in Neurobiology*, 71: 385-400 (2003).

Stein et al., "Neutralization of Transthyretin Reverses the Neuroprotective Effects of Secreted Amyloid Precursor Protein (APP) in $APP_{sw}$ Mice Resulting in Tau Phosphorylation and Loss of Hippoampal Neurons: Support for the Amyloid Hypothesis," *The Journal of Neuroscience*, 24(35): 7707-7717 (Sep. 1, 2004).

Tsuzuki et al., "Transthyretin Binds Amyloid β Peptides, Aβ1-42 and Aβ1-40 to Form Complex in the Autopsied Human Kidney—Possible Role of Transthyretin for Aβ Sequestration," *Neuroscience Letters*, 281(2/3): 171-174 (2000).

Vinceti et al., "Lead, Cadmium, and Selenium in the Blood of Patients With Sporadic Amyotrophic Lateral Sclerosis," *The Italian Journal of Neurological Sciences*, 18(2): 8792 (Apr. 2, 1997).

Zheng et al, "Transthyretin, Thyroxine, and Retinol-Binding Protein in Human Cerebrospinal Fluid: Effect of Lead Exposure," *Toxicological Sciences*, 61: 107-114 (2001).

Zheng, "Toxicology of Choroid Plexus: Special Reference to Metal-Induced Neurotoxicities," *Microscopy Research and Technique*, 52: 89-103 (2001).

Zhu et al., "Internal Cleavage of the Inhibitory 7B2 Carboxyl-Terminal Peptide by PC2: A Potential Mechanism for its Inactivation," *Proceedings of the National Academy of Sciences of the Untied States of America*, 93(10): 4919-4924 (May 1996).

* cited by examiner

BIOMARKERS FOR AMYOTROPHIC LATERAL SCLEROSIS

CROSS-REFERENCE TO RELATED PATENT APPLICATIONS

This patent application claims the benefit of U.S. Provisional Patent Application No. 60/513,930, filed Oct. 23, 2003.

STATEMENT REGARDING FEDERALLY SPONSORED RESEARCH AND DEVELOPMENT

This invention was made in part with Government support under Grant Number ES013469 awarded by the National Institute of Environmental Health Sciences. The Government may have certain rights in this invention.

FIELD OF THE INVENTION

This invention pertains to biomarkers of amyotrophic lateral sclerosis and methods of using same.

BACKGROUND OF THE INVENTION

Amyotrophic lateral sclerosis (ALS), also known as Lou Gehrig's disease or motor neuron disease (MND), is one of several neurodegenerative diseases of the central nervous system. ALS is the most common adult onset motor neuron disease, affecting one in every 20,000 individuals, with an average age of onset of 50-55 years. ALS is characterized by rapidly progressive degeneration of motor neurons in the brain, brainstem, and spinal cord (Cleveland et al., *Nat. Rev. Neurosci.*, 2, 806-19 (2001)). The median survival of patients from time of diagnosis is five years.

ALS exists in both sporadic and familial forms. Familial ALS (FALS) comprises only 5-10% of all ALS cases. Over the last decade, a number of basic and clinical research studies have focused on understanding the familial form of the disease, which has led to the identification of eight genetic mutations related to FALS. Transgenic mice expressing point mutants of the Cu/Zn superoxide dismutase-1 (SOD1) gene develop an age-dependent progressive motor weakness similar to human ALS due to a toxic gain of function (Rosen et al., *Nature*, 362, 59-62 (1993), Rosen et al. *Hum Mol Genet*, 3, 981-987 (1994), and Borchelt et al., *Proc. Natl. Acad. Sci. USA*, 91, 8292-8296 (1994)).

These genetic mutations, however, do not explain sporadic ALS (SALS). The pathogenesis of SALS is multifactorial. A number of different model systems, including SOD1 transgenic mice, in vitro primary motor neuron cultures or spinal cord slice cultures, in vivo imaging studies, and postmortem examination of tissue samples, have been utilized to understand the pathogenesis of ALS (Subramaniam et al., *Nat. Neurosci.*, 5, 301-307 (2002), Nagai et al., *J. Neurosci.*, 21, 9246-9254 (2001), Menzies et al. *Brain*, 125, 1522-1533 (2002), Kim et al. *J. Neuropathol. Exp. Neurol.*, 62, 88-103 (2003), and Ranganathan et al., *Am. J. Pathol.*, 162, 823-835 (2003)). Although these studies have yielded therapeutic targets and several clinical trials, there are no drugs that delay disease onset or prolong long-term survival of ALS patients. Riluzole (Rilutek®, Aventis), a glutamate antagonist, currently is the only FDA-approved medication available to treat ALS. Riluzole, however, extends life expectancy by only a few months (Miller et al., *Amyotrophic Lateral Sclerosis & Other Motor Neuron Disorders*, 4, 191-206 (2003)). Creatine and α-tocopherol have shown some efficacy in relieving the symptoms of ALS in SOD1 transgenic mice, but exhibit minimal efficacy in human ALS patients (Groeneveld et al., *Annals of Neurology*, 53, 437-45 (2003), and Desnuelle et al., *Amyotrophic Lateral Sclerosis & Other Motor Neuron Disorders*, 2, 9-18 (2001)).

There remains a need for improved methods for identifying therapeutic targets of ALS, and improved methods of diagnosing the disease. The invention provides such methods.

BRIEF SUMMARY OF THE INVENTION

The invention provides a method for diagnosing amyotrophic lateral sclerosis (ALS) in a subject. The method comprises (a) obtaining a sample from the subject, (b) analyzing the proteins in the sample by mass spectroscopy, (c) determining a mass spectral profile for the sample, and (d) comparing the mass spectral profile of the sample to the mass spectral profile of a positive or a negative standard.

The invention also provides a method for assessing the effectiveness of a drug in treating amyotrophic lateral sclerosis. The method comprises (a) obtaining a first sample from a subject suffering from amyotrophic lateral sclerosis, (b) analyzing the proteins in the first sample by mass spectroscopy, (c) determining a mass spectral profile for the first sample, (d) administering the drug to the subject, (e) obtaining a second sample from the subject after completion of step (d), (f) analyzing the proteins in the second sample by mass spectroscopy, (g) determining a mass spectral profile for the second sample, and (h) comparing the mass spectral profile of the first sample to the mass spectral profile of the second sample.

Further provided is a method for determining the site of onset of amyotrophic lateral sclerosis (ALS) in a subject. The method comprises (a) obtaining a sample from the subject, (b) analyzing the proteins in the sample by mass spectroscopy, (c) determining a mass spectral profile for the sample, wherein (i) a mass spectral profile comprising one or more biomarkers selected from the group consisting of a 3.26 kDa protein peak, a 3.44 kDa protein peak, and a 7.5 kDa protein peak indicates onset of ALS in a limb of the subject, and (ii) a mass spectral profile comprising one or more biomarkers selected from the group consisting of a 2.4 kDa protein peak, a 6.4 kDa protein peak, a 12.1 protein peak, a 12.2 kDa protein peak, a 12.2 kDa protein peak, a 14.1 kDa protein peak, and a 15.9 kDa protein peak indicates onset of ALS in the bulbar region of the subject.

These and other advantages of the invention, as well as additional inventive features, will be apparent from the description of the invention provided herein.

DETAILED DESCRIPTION OF THE INVENTION

Figure 1:
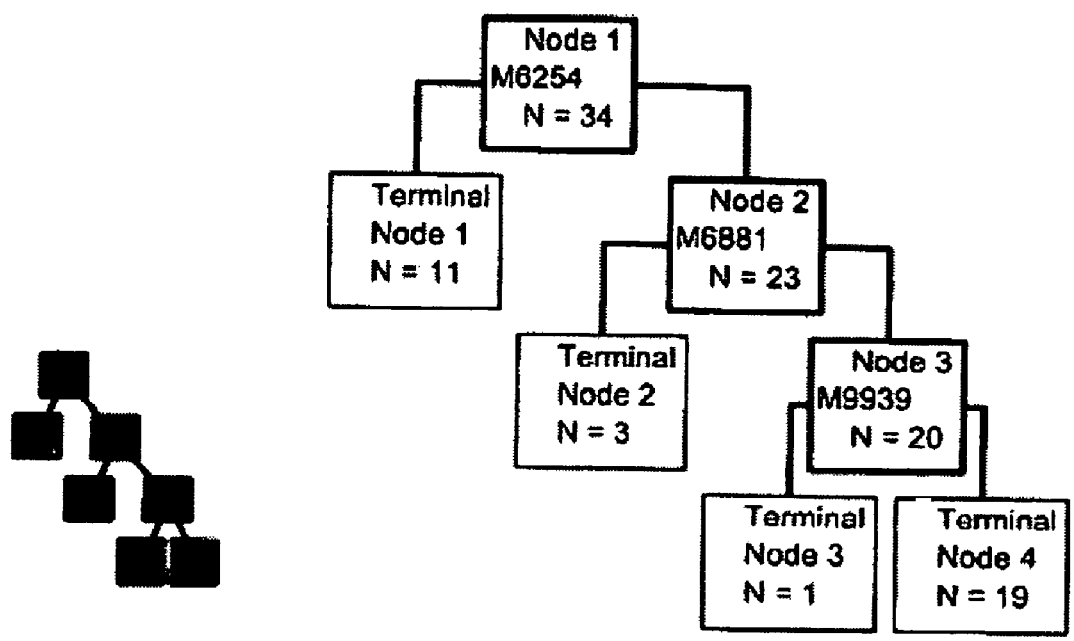
FIG. 1 is a diagram depicting a classification tree generated by Ciphergen Biomarker Patterns Software for the diagnosis of ALS using a SAX2 ProteinChip®.

The present invention provides a method for diagnosing amyotrophic lateral sclerosis (ALS) in a subject. The method comprises (a) obtaining a sample from the subject, (b) analyzing the proteins in the sample by mass spectroscopy, (c) determining a mass spectral profile for the sample, and (d) comparing the mass spectral profile of the sample to the mass spectral profile of a positive or a negative standard.

The term "sample," as used herein, refers to biological material isolated from a subject. The subject can be any suitable animal, but preferably is a mammal, such as a mouse, rat, monkey, or human. It is contemplated that the aforementioned inventive method can be used to diagnose ALS in animal models of the disease, in which case the subject is a non-human animal (e.g., a mouse, rat, monkey, dog, etc.). In a preferred embodiment, the subject is a human. The sample can contain any suitable biological material, but preferably comprises cells obtained from a particular tissue or biological fluid. The sample can be isolated from any suitable tissue or biological fluid. In this respect, the sample can be blood, blood serum, plasma, or urine. In that ALS affects the central nervous system, the sample preferably is isolated from tissue or biological fluid of the central nervous system (CNS) (i.e., brain and spinal cord). In a particularly preferred embodiment of the invention, the sample is isolated from cerebrospinal fluid (CSF). CSF cushions the brain and spinal cord, regulates brain extracellular fluid, allows for distribution of neuroactive substances, and collects the waste products produced by the brain. CSF flows through the skull and spine in the subarachnoid space, which is the area inside the arachnoid membrane. Numerous metabolites from neurons and glial cells from the CNS are secreted into the CSF. Thus, CSF reflects the metabolic state of the brain. Moreover, CSF from ALS patients has been used for biochemical assays that have identified changes in the levels of glutamate, glutamine synthetase, transglutaminase activity, γ-aminobutyric acid, and various markers of oxidative injury (see, e.g., Spreux-Varoquaux et al., *Journal of the Neurological Sciences*, 193, 73-78 (2002), Shaw et al., *Amyotrophic Lateral Sclerosis & Other Motor Neuron Disorders*, 1, Suppl. 2, S61-67 (2000), and Smith et al., *Ann. Neurol.*, 44, 696-699 (1998)).

The sample can be obtained in any suitable manner known in the art, such as, for example, by biopsy, blood sampling, urine sampling, lumbar puncture (i.e., spinal tap), ventricular puncture, and cisternal puncture. In a preferred embodiment of the invention, the sample is obtained by lumbar puncture, which also is referred to as a spinal tap or cerebrospinal fluid collection. Lumbar puncture involves insertion of a spinal needle, usually between the 3rd and 4th lumbar vertebrae, into the subarachnoid space where CSF is collected. In instances where there is lumbar deformity or infection which would make lumbar puncture impossible or unreliable, the sample can be collected by ventricular puncture or cisternal puncture. Ventricular puncture typically is performed in human subjects with possible impending brain herniation. Ventricular puncture involves drilling a hole in the skull and inserting a needle directly into the lateral ventricle of the brain to collect CSF. Cisternal puncture involves insertion of a needle below the occipital bone (back of the skull), and can be hazardous due to the proximity of the needle to the brain stem.

Many neurodegenerative diseases, such as Alzheimer's disease, Parkinson's disease, Huntington's disease, and ALS are characterized by the accumulation or presence of protein abnormalities which contribute to the disease phenotype, and are thus sometimes referred to in the art as "proteinopathies" (Jellinger, *Movement Disorders*, 18, Suppl 6, S2-12 (2003), and Paulson, *American Journal of Human Genetics*, 64, 339-45 (1999)). The collection of all of the proteins and peptide sequences present within a biological sample at a given time often is referred to in the art as the "proteome." Thus, the inventive method provides a means to analyze the proteome of a particular sample. One of ordinary skill in the art will appreciate that a proteomic analysis of the proteins present in a biological sample involves the systematic separation, identification, and characterization of all peptide sequences within the sample. The proteins in the sample can be separated by any suitable method known in the art. Suitable methods include, for example, centrifugation, ion exchange chromatography, reversed-phase liquid chromatography, and gel electrophoresis. Preferably, the proteins in the sample are separated using gel electrophoresis (e.g., one-dimensional or two-dimensional gel electrophoresis). Most preferably, the proteins in the sample are separated by subjecting the sample to two-dimensional gel electrophoresis (2DGE). 2DGE typically involves separation of proteins in a first dimension by charge using isoelectric focusing (IEF). The charge-focused proteins are then separated in a second dimension according to size by using an SDS-polyacrylamide gel (see, e.g., Lin et al., *Biochimica et Biophysica Acta*, 1646, 1-10 (2003), and Ong et al., *Biomol. Eng.*, 18, 195-205 (2001)).

Following separation of the proteins in the sample, each of the proteins can be isolated from the separation medium. The proteins can be isolated using any suitable technique, such as by extracting the protein "spots" from the gel. Extraction of protein spots from a gel typically involves the physical cutting of the spot from the gel.

Once the proteins in the sample are separated, the inventive method comprises analyzing the proteins in the sample by mass spectroscopy. In mass spectroscopy, a substance is bombarded with an electron beam having sufficient energy to fragment the molecule. The positive fragments that are produced (cations and radical cations) are accelerated in a vacuum through a magnetic field and are sorted on the basis of mass-to-charge ratio (m/z). Since the bulk of the ions produced in the mass spectrometer carry a unit positive charge, the value m/z typically is equivalent to the molecular weight of the fragment. Any suitable mass spectroscopy method can be used in connection with the inventive method. Examples of suitable mass spectroscopy methods include matrix-assisted laser desorption/ionization mass spectroscopy (MALDI), matrix-assisted laser desorption/ionization-time of flight (MALDI-TOF) mass spectroscopy, plasma desorption/ionization mass spectroscopy (PDI), electrospray ionization mass spectroscopy (ESI), and surface enhanced laser desorption/ionization-time of flight (SELDI-TOF) mass spectroscopy. In time-of-flight (TOF) methods of mass spectroscopy, charged (ionized) molecules are produced in a vacuum and accelerated by an electric field produced by an ion-optic assembly into a free-flight tube or drift time. The velocity to which the molecules may be accelerated is proportional to the square root of the accelerating potential, the square root of the charge of the molecule, and inversely proportional to the square root of the mass of the molecule. The charged molecules travel down the TOF tube to a detector. Mass spectroscopy methods are further described in, for example, International Patent Application Publication No. WO 93/24834, U.S. Pat. No. 5,792,664, U.S. Patent Application Publication No. 2004/0033530 A1, and Hillenkamp et al., *Matrix Assisted UV-Laser Desorption/Ionization: A New Approach to Mass Spectroscopy of Large Biomolecules, Biological Mass Spectroscopy*, Burlingame and McCloskey, eds., Elsevier Science Publ., pp. 49-60 (1990).

In a preferred embodiment of the invention, the proteins in the sample are analyzed by SELDI-TOF mass spectroscopy. Surface enhanced desorption/ionization processes refer to those processes in which the substrate on which the sample is presented to the energy source plays an active role in the desorption/ionization process. In this respect, the substrate (e.g., a probe) is not merely a passive stage for sample presentation. Several types of surface enhanced substrates can be employed in a surface enhanced desorption/ionization process. In one embodiment, the surface comprises an affinity material, such as anion exchange groups or hydrophilic groups (e.g., silicon oxide), which preferentially bind certain classes of molecules. Examples of such affinity materials include, for example, silanol (hydrophilic), $C_8$ or $C_{16}$ alkyl (hydrophobic), immobilized metal chelate (coordinate covalent), anion or cation exchangers (ionic) or antibodies (biospecific). The sample is exposed to a substrate bound adsorbent so as to bind analyte molecules according to the particular basis of attraction. When the analytes are biomolecules (e.g., proteins), an energy absorbing material (e.g., matrix) typically is associated with the bound sample. A laser is then used to desorb and ionize the analytes, which are detected with a detector. For SELDI-TOF mass spectroscopy, the mass accuracy for each protein peak is +/−0.2%. SELDI-TOF mass spectroscopy systems are commercially available from, for example, Ciphergen Biosystems, Inc. (Fremont, Calif.). Surface enhanced desorption/ionization methods are described in, e.g., U.S. Pat. Nos. 5,719,060, 6,294,790, and 6,675,104, and International Patent Application Publication No. WO 98/59360.

One of ordinary skill in the art will appreciate that the output of a mass spectroscopy analysis is a plot of relative intensity as a function of the mass-to-charge ratio (m/z) of the proteins in the sample, which is referred to as a "mass spectral profile" or "mass spectrum." The mass spectral profile, which typically is represented as a histogram depicting protein "peaks," serves to establish the molecular weight and structure of the compound being analyzed. Thus, the inventive method further comprises determining a mass spectral profile for the sample. The most intense peak in the spectrum is termed the base peak, and all other peaks are reported relative to the intensity of the base peak. The peaks themselves are typically very sharp, and are often simply represented as vertical lines.

The ions that are formed by fragmentation of the proteins in the sample during mass spectroscopy are the most stable cations and radical cations formed by the protein molecules. The highest molecular weight peak observed in a spectrum typically represents the parent molecule less an electron, and is termed the molecular ion (M+). Generally, small peaks are also observed above the calculated molecular weight due to the natural isotopic abundance of $^{13}C$, $^2H$, etc. Many molecules with especially labile protons do not display molecular ions. For example, the highest molecular weight peak in the mass spectrum of alcohols occurs at an m/z one less than the molecular ion (m-1). Fragments can be identified by their mass-to-charge ratio, but it is often more informative to identify them by the mass which has been lost. For example, loss of a methyl group will generate a peak at m-15, while loss of an ethyl will generate a peak at m-29.

The inventive method further comprises comparing the mass spectral profile of the sample to the mass spectral profile of a positive or a negative standard. By "standard" is meant a sample that permits the identification, quantification, and/or characterization of other molecules (e.g., proteins). With respect to methods of diagnosing a disease, a standard is "positive" when it comprises molecules that are indicators of a particular disease, or disease progression. Such indicator molecules also are referred to as "biomarkers," and typically are proteins or protein fragments. A standard is "negative" when it lacks molecules that are indicators of a particular disease or disease progression, or comprises molecules indicative of a subject without a particular disease. In the context of the inventive method, the standard facilitates a positive or negative diagnosis of ALS. The standard can be any positive or negative standard, so long as the sample and the standard can be effectively compared so as to arrive at a particular diagnosis for ALS, in accordance with the inventive method. In a preferred embodiment of the invention, the positive standard comprises a sample obtained from a subject suffering from ALS. In contrast, a negative standard preferably comprises a sample (e.g., a human) obtained from a subject that does not suffer from ALS.

When the standard is a positive standard obtained from a subject suffering from ALS, the mass spectral profile of the standard can comprise any suitable number of biomarkers that will enable a clinician to make a reliable diagnosis. The mass spectral profile of the positive standard preferably comprises one or more biomarkers selected from the group consisting of a 2.01 kilodalton (kDa) protein peak, a 2.16 kDa protein peak, a 2.2 kDa protein peak, a 2.4 kDa protein peak, a 2.46 kDa protein peak, a 2.66 kDa protein peak, a 2.7 kDa protein peak, a 3.01 kDa protein peak, a 3.3 kDa protein peak, a 3.42 kDa protein peak, a 3.7 kDa protein peak, a 3.8 kDa protein peak, a 4.4 kDa protein peak, a 4.8 kDa protein peak, a 4.9 kDa protein peak, a 5.1 kDa protein peak, a 5.4 kDa protein peak, a 5.8 kDa protein peak, a 6.2 kDa protein peak, a 6.5 kDa protein peak, a 6.7 kDa protein peak, a 6.86 kDa protein peak, a 6.88 kDa protein peak, a 7.02 kDa protein peak, a 7.74 kDa protein peak, a 7.77 kDa protein peak, an 8.2 kDa protein peak, an 8.6 kDa protein peak, an 8.93 kDa protein peak, a 9.1 kDa protein peak, a 10.15 kDa protein peak, a 10.64 kDa protein peak, a 10.9 kDa protein peak, an 11.5 kDa protein peak, a 12.05 kDa protein peak, a 12.09 kDa protein peak, a 12.28 kDa protein peak, a 12.8 kDa protein peak, a 13.1 kDa protein peak, a 13.3 kDa protein peak, a 13.65 kDa protein peak, a 13.68 kDa protein peak, a 13.7 kDa protein peak, a 14.6 kDa protein peak, a 15.2 kDa protein peak, a 15.6 kDa protein peak, a 16.7 kDa protein peak, and a 17.1 kDa protein peak. The presence of the aforementioned biomarkers can be associated with abnormalities in protein expression levels (e.g., as a result of protein overexpression), abnormal proteolytic processing, and abnormal post-translational modification of proteins (e.g., glycosylation or oxidation).

Thus, in accordance with the inventive method, a positive diagnosis of ALS occurs when the mass spectral profile of a sample obtained from a subject of interest (e.g., a human) comprises one or any combination of the biomarkers observed in the mass spectral profile of a positive standard as described above. In this respect, a positive diagnosis of ALS can be made when the mass spectral profile of a sample obtained from a subject comprises two or more, three or more, four or more, or even five or more (e.g., 6, 7, 8, 9, 10, or 15) of the protein peaks distinct for a positive standard as set forth above. Indeed, particular subsets of the protein peaks set forth above can have diagnostic significance with respect to ALS. Such a subset preferably includes a 2.4 kDa a protein peak, a 2.46 kDa protein peak, a 3.01 kDa protein peak, a 6.88 kDa protein peak, a 7.77 kDa protein peak, a 8.9 kDa protein peak, and a 13.65 kDa protein peak, which subset provides 100% accuracy of diagnosing ALS. Alternatively, the subset includes a 2.4 kDa protein peak, a 3.01 kDa protein peak, a 4.8 kDa protein peak, a 6.86 kDa protein peak, a 7.74 kDa protein peak, a 8.93 kDa protein peak, and a 13.1 kDa protein peak, which subset provides 100% accuracy of diagnosing ALS. These subsets, however, are merely exemplary, and any suitable subset of the biomarkers identified herein can be used to diagnose ALS. In addition, the positive diagnosis of ALS can be confirmed by comparing the mass spectral profile of the sample to the mass spectral profile of a negative standard. In this respect, the positive diagnosis is confirmed when the mass spectral profile of the negative standard does not comprise any of the biomarkers observed in the mass spectral profile of the sample of the subject (e.g., a human).

Likewise, a negative diagnosis of ALS (i.e., a subject does not have ALS) occurs when the mass spectral profile of a sample obtained from a subject of interest (e.g., a human) is substantially the same as the mass spectral profile of a negative standard as described above. The negative diagnosis of ALS can be confirmed by comparing the mass spectral profile of the sample to the mass spectral profile of a positive standard. In this respect, the negative diagnosis of ALS is confirmed when the mass spectral profile of the sample of the subject of interest does not comprise any of the biomarkers observed in the mass spectral profile of a positive standard as described above. Alternatively, a negative diagnosis of ALS can be confirmed using a specific subset of biomarkers distinct for a negative standard.

One of ordinary skill in the art will appreciate that any one or combination (i.e., subset) of protein peaks identified in the sample obtained from a subject of interest can be exclusive to a positive or negative standard. Alternatively, the intensity value of the protein peaks in the sample can provide the diagnostic information when compared to a positive and/or negative standard. In other words, the average protein peak intensity values can differentiate a patient having ALS and a patient that does not have ALS. In one embodiment, any one subject does not contain all of the protein peaks diagnostic for ALS in a positive standard or all the protein peaks specific to a negative standard, but can still be diagnosed as having ALS or not having ALS in accordance with the inventive method. For example, a sample obtained from a human can contain one protein peak indicative of ALS, but four protein peaks indicative of a negative standard, and therefore can be negatively diagnosed (i.e., the individual does not have ALS).

As discussed above, the diagnosis of ALS in a subject does not require that all of the biomarkers in the positive standard be present in the sample obtained from a patient of interest. Indeed, a diagnosis of ALS can be made if a sample obtained from the patient comprises any one, a combination of biomarkers in the positive standard, or a specific subset of biomarkers distinct for the positive standard. In addition, a diagnosis of ALS can be made if a sample obtained from the subject comprises one or more fragments or full-length amino acid sequences of the biomarkers in the positive standard. Moreover, as a result of post-translational modification of proteins, it is also contemplated that a diagnosis of ALS can be made when the sample obtained from a subject comprises a modified form (e.g., a glycosylated form) of one or more of the biomarkers in the positive standard.

One of the goals of protein mass spectroscopy is protein identification. Thus, the inventive method also encompasses the identification of the protein biomarkers from a particular sample. In this respect, the proteins can be identified using any suitable protein identification method known in the art. Suitable protein identification methods include, for example, protein electroblotting, Edman sequencing (see, e.g., Gevaert et al., *Electrophoresis,* 21, 1145-1154 (2000)), and sequencing by mass spectroscopy (see, e.g., Kinter and Sherman, *Protein Sequencing and Identification Using Tandem Mass Spectroscopy*, Wiley-Interscience (2000), and U.S. Pat. Nos. 6,632,339 and 6,706,529). Mass spectroscopy-based protein identification methods include, for example, MALDI-MS peptide mass fingerprinting (MALDI-MS-PMF) and MALDI-MS post-source decay analysis (MALDI-MS-PSD). In MALDI-MS-PMF, a protein of interest, which typically is purified by 2-D gel electrophoresis, is either enzymatically or chemically cleaved and an aliquot of the obtained peptide mixture is analyzed by mass spectrometric techniques, thereby generating a mass "fingerprint" of the protein. The mass fingerprint is subsequently compared to "virtual" fingerprints obtained by theoretical cleavage of protein sequences stored in databases (e.g., MOWSE, ProFound, PeptIdent, and PeptideSearch), and the top scoring proteins are retrieved as possible candidate proteins (see, e.g., Gevaert et al., supra). PSD fragments are generated in the field-free drift region after MALDI. It has been postulated that PSD primarily is the result of amide bond cleavages. Due to the high complexity of PSD spectra, however, MALDI-MS-PSD is not frequently in the art to identify proteins (see, e.g., Gevaert et al., supra). In a preferred embodiment of the invention, the proteins in a sample are identified by MALDI-MS-PMF. Upon preliminary identification of a protein in a sample, the identity of the protein can be confirmed by various protein detection methods known in the art, such as, for example, enzyme-linked immunosorbent assay (ELISA), Western blot analysis, immunoprecipitation, and isoelectric focusing followed by 2-D gel electrophoresis.

In one embodiment of the invention, the 3.42 kDa, 13.3 kDa, and 13.7 kDa protein peaks of the positive standard correspond to a 7B2 protein, a cystatin C protein, and a transthyretin protein, respectively, or a fragment or variant thereof (e.g., a C-terminal fragment of a 7B2 protein). The 7B2 protein is a neuroendocrine pituitary protein, and is further described in Martens, *FEBS Lett.,* 234, 160-164 (1988). Cystatin C is a human cysteine proteinase inhibitor, which has been associated with hereditary amyloid angiopathy (see, e.g., Levy et al., *J. Exp. Med.,* 169, 1771-1778 (1989)). The cDNA sequence coding for a precursor of human cystatin C is disclosed in Abrahamson et al., *FEBS Lett.,* 216, 229-233 (1987). Transthyretin (also called prealbumin) is a tetrameric human plasma protein known to transport thyroxine and retinol. It is the major component of familial amyloidotic plyneuropathy (FAP) amyloid fibrils, and has approximately sixty amyloidogenic mutational variants. The nucleotide sequence encoding transthyretin is disclosed in Tsuzuki et al., *J. Biol. Chem.,* 260, 12224-7 (1985), while the amino acid sequence of transthyretin is disclosed in, for example, Mita et al., *Biochem. Biophys. Res. Commun.,* 124, 558-64 (1984).

The invention further provides a method for assessing the effectiveness of a drug in treating amyotrophic lateral sclerosis in a subject. The method comprises (a) obtaining a first sample from a subject suffering from amyotrophic lateral sclerosis, (b) analyzing the proteins in the first sample by mass spectroscopy, (c) determining a mass spectral profile for the first sample, (d) administering the drug to the subject, (e) obtaining a second sample from the subject after administering the drug thereto, (f) analyzing the proteins in the second sample by mass spectroscopy, (g) determining a mass spectral profile for the second sample, and (h) comparing the mass spectral profile of the first sample to the mass spectral profile of the second sample, wherein the effectiveness of the drug is assessed. Descriptions of the sample, mass spectrometric analysis of the sample, and the mass spectral profile of the sample set forth above in connection with other embodiments of the invention also are applicable to those same aspects of the aforesaid inventive method for assessing the effectiveness of a drug. In addition to ALS, the inventive method for assessing the effectiveness of a drug can be used to assess the effectiveness of a drug in treating any suitable motor neuron disease in a subject. Suitable motor neuron diseases include, for example, progressive bulbar palsy, progressive muscular atrophy, primary lateral sclerosis, and postpolio syndrome.

The drug can be administered to the subject in any suitable manner depending on whether local or systemic treatment is desired, and on the area to be treated. Administration can be topical (including ophthalmical, vaginal, rectal, intranasal, transdermal, and the like), oral, by inhalation, or parenteral (including by intravenous drip or subcutaneous, intracavity, intraperitoneal, or intramuscular injection). Delivery can also be directly to any area of the respiratory system (e.g., lungs) via intubation. The drug preferably is administered to the subject orally. Compositions for oral administration include powders or granules, suspensions or solutions in water or non-aqueous media, capsules, sachets, or tablets.

The inventive method can be used to assess the effectiveness of any drug suitable for the treatment of ALS. Suitable drugs include those currently commercially available, such as Riluzole (Rilutek®, Aventis), and those yet to be developed. It will be apparent to one of ordinary skill in the art that a drug which is active against ALS will ameliorate or eliminate the symptoms of ALS, most likely by restoring normal protein expression levels, normal post-translational protein modification, and/or normal protein processing. Thus, the mass spectral profile of the first sample isolated from a subject suffering from ALS will be altered as a result of drug administration. Accordingly, a drug is deemed effective in treating ALS, or other motor neuron disease, when the mass spectral profile of the second sample isolated from the subject does not comprise one or more of the biomarkers or subsets of biomarkers present in the mass spectral profile of the first sample, or does not exhibit any new protein peaks characteristic of disease progression. For example, when the mass spectral profile of the first sample contains three of the biomarker protein peaks described herein, a drug that is effective in treating ALS can alter the mass spectral profile of the first sample such that the mass spectral profile of the second sample contains, one, two, or none of the biomarkers present in the first sample. In contrast, a drug that is not effective against ALS likely will not restore normal protein expression levels, normal post-translational modification, and/or normal protein processing. Thus, in the context of the invention, a drug is deemed ineffective in treating ALS when the mass spectral profile of the second sample isolated from the subject comprises all of the biomarkers present in the first sample.

The mass spectral profile of the first sample can comprise any suitable number of biomarkers of ALS described herein. The mass spectral profile of the first sample preferably comprises one or more biomarkers selected from the group consisting of 2.01 kilodalton (kDa) protein peak, a 2.16 kDa protein peak, a 2.2 kDa protein peak, a 2.4 kDa protein peak, a 2.46 kDa protein peak, a 2.66 kDa protein peak, a 2.7 kDa protein peak, a 3.01 kDa protein peak, a 3.3 kDa protein peak, a 3.42 kDa protein peak, a 3.7 kDa protein peak, a 3.8 kDa protein peak, a 4.4 kDa protein peak, a 4.8 kDa protein peak, a 4.9 kDa protein peak, a 5.1 kDa protein peak, a 5.4 kDa protein peak, a 5.8 kDa protein peak, a 6.2 kDa protein peak, a 6.5 kDa protein peak, a 6.7 kDa protein peak, a 6.86 kDa protein peak, a 6.88 kDa protein peak, a 7.02 kDa protein peak, a 7.74 kDa protein peak, a 7.77 kDa protein peak, an 8.2 kDa protein peak, an 8.6 kDa protein peak, an 8.93 kDa protein peak, a 9.1 kDa protein peak, a 10.15 kDa protein peak, a 10.64 kDa protein peak, a 10.9 kDa protein peak, an 11.5 kDa protein peak, a 12.05 kDa protein peak, a 12.09 kDa protein peak, a 12.28 kDa protein peak, a 12.8 kDa protein peak, a 13.1 kDa protein peak, a 13.3 kDa protein peak, a 13.65 kDa protein peak, a 13.68 kDa protein peak, a 13.7 kDa protein peak, a 14.6 kDa protein peak, a 15.2 kDa protein peak, a 15.6 kDa protein peak, a 16.7 kDa protein peak, and a 17.1 kDa protein peak. The mass spectral profile of the first sample obtained from a subject of interest can comprise one biomarker, combination of biomarkers, or subset of biomarkers (or combination of subsets) of biomarkers observed in the mass spectral profile of a positive standard as described herein.

The invention further provides a method for determining the site of onset of amyotrophic lateral sclerosis (ALS) in a subject. The method comprises (a) obtaining a sample from the subject, (b) analyzing the proteins in the sample by mass spectroscopy, and (c) determining a mass spectral profile for the sample. A mass spectral profile comprising one or more biomarkers selected from the group consisting of a 3.26 kDa protein peak, a 3.44 kDa protein peak, and a 7.5 kDa protein peak indicates onset of ALS in a limb of the subject, while a mass spectral profile comprising one or more biomarkers selected from the group consisting of a 2.4 kDa protein peak, a 6.4 kDa protein peak, a 12.1 protein peak, a 12.2 kDa protein peak, a 14.1 kDa protein peak, and a 15.9 kDa protein peak indicates onset of ALS in the bulbar region of the subject. Descriptions of the sample, mass spectrometric analysis of the sample, and the mass spectral profile of the sample set forth above in connection with other embodiments of the invention also are applicable to those same aspects of the aforesaid inventive method for determining the site of onset of ALS. Limb-onset ALS occurs when the first symptoms of ALS in a human arise in the arms or legs, and occurs in the majority of ALS patients. Bulbar-onset ALS occurs when the first symptoms of ALS in a human arise in the bulbar region, which includes the region of the brain stem comprising the cerebellum, medulla, and pons, and typically presents as difficulty swallowing or speaking.

As discussed above, the determination of the site of ALS onset in a subject does not require that all of the above-described biomarkers be present in the sample obtained from a subject of interest. Indeed, a determination of the site of ALS onset can be made if a sample obtained from the patient comprises any one, combination of, or subset of the above-described biomarkers. In addition, a determination of the site of ALS onset can be made if a sample obtained from the patient comprises one or more fragments or full-length amino acid sequences of the biomarkers in the positive standard. Moreover, as a result of post-translational modification of proteins, it is also contemplated that determination of the site of ALS onset can be made when the sample obtained from a patient comprises a modified form (e.g., a glycosylated form) of one or more of the biomarkers.

The following examples further illustrate the invention but, of course, should not be construed as in any way limiting its scope.

EXAMPLES

General Procedures

Subjects

A study population was assembled, which included 15 subjects with a recent clinical diagnosis of ALS performed by board certified neurologists specializing in motor neuron disease. While 14 of the patients were sporadic ALS cases, one patient was a familial case with no mutation in the SOD1 gene. The average age of these patients was 49.6±3.4 years (n=15). Some of the ALS patients had been treated with Riluzole, creatine, anti-oxidants, or a combination of these compounds. The control group included 24 subjects with an average age of 46.7±3.8 years (n=24). The control patients were age-matched to the ALS group and were not statistically significant (p=0.44) when analyzed using an unpaired student t test. A blinded set of 20 patients also was used for this study.

Sample Preparation

Human CSF was obtained through lumbar punctures and immediately centrifuged at 1500 rpm for five minutes at 4° C. to remove any cellular debris. The supernatant was aliquoted and frozen at −80° C. Samples were thawed on ice prior to use. Protein concentrations in the CSF samples were determined using the Bradford assay (Bradford, *Anal. Biochem*, 72, 248 (1976)). The protein concentration varied from 0.15 µg/µl to 0.8 µg/µl. In all experiments 10 µg of protein was utilized to spot on chip arrays (described below).

Mass Spectroscopy

Mass spectroscopy was performed using SELDI Protein-Chip® technology (Ciphergen Biosystems, Inc., Fremont, Calif.). A total of four chip types were used to assay human CSF samples: H4 (hydrophobic surface), SAX2 (strong anion exchange surface), WCX2 (weak cation exchange surface), and IMAC3 (immobilized metal binding surface) and multiple pH binding conditions. Two protein chip arrays, SAX2 (strong anionic exchange) and IMAC3 (immobilized metal affinity chip) exhibited the best spectral data for CSF and were utilized for further analyses. The spots on SAX2 chips were equilibrated with 100 mM Tris-HCl pH 8.5, and the fractionated samples were added to the spots. The IMAC3 arrays were treated with 100 mM zinc sulfate or 100 mM copper sulfate followed by washing with 50mM sodium acetate. These were then repeatedly washed with HPLC grade water and phosphate buffered saline. 10 µg of CSF samples were diluted in 1% triflouroacetic acid (TFA) such that the final concentration of TFA was 0.1%. Samples were fractionated using C4 ZipTip pipette tips (Millipore) according to the manufacturer's instructions. Samples were then mixed onto the SELDI target chip surface with a saturated matrix solution of 4-hydroxy-α-cinnamic acid (sinapinic acid). The matrix was prepared as a saturated, aqueous solution containing 50% (v/v) acetonitrile Can) in HPLC grade water (Sigma, St. Louis, Mo.) and 0.3% (v/v) trifluoroacetic acid (TFA). The samples were evaporated at room temperature before acquiring protein-pro filing spectra using SELDI-TOF (Ciphergen Biosystems, Inc., Fremont, Calif.) For each individual experiment, all CSF samples were analyzed in duplicate (i.e., two separate wells on two different ProteinChips) to demonstrate reproducibility of the results.

In addition, three separate experimental runs for each ProteinChip were performed. Therefore, each sample was analyzed in duplicate within each experiment, and each experiment was repeated three times. For each experiment, one CSF sample was used as an internal standard to compare peak intensities from four selected m/z peaks to measure variability of the mass spectra. The coefficient of variance (CV) for these selected peaks was less than 25%.

External calibration of the Protein Chip Reader was performed using the Ciphergen All-in-One peptide/protein standard mix containing peptides ranging from 1000 Da to 20 kDa. The dried chips were immediately loaded into the calibrated Chip Reader using optimal laser intensity and detector sensitivity with a mass deflector setting of 1000 Da for low mass range (2-20 kDa) and 10,000 kDa for high mass range (20 kDa-80 kDa). These settings were kept constant for all the chips of every experiment. The mass/charge (m/z) ratios were determined using time of flight (TOF) analysis. These spectras were collected with a Protein Chip system (PBS II series; Ciphergen Biosystems Inc., Palo Alto).

Data Analysis

Protein peaks were analyzed with the Ciphergen Biomarker Patterns Software (BPS) package version 3.1 licensed by Ciphergen Biosystems, and the Rules Learning (RL) Parameters algorithm. BPS is a classification algorithm defining pattern recognition approach and building classification trees. Each tree comprises a parent node and branch nodes or terminal nodes. There is a relative cost value associated with each of these trees. The algorithm also calculates values for sensitivity and specificity of the peaks. Sensitivity is defined as the ratio of the number of correctly classified disease cases to total number of disease cases. Specificity is defined as the ratio of the number of correctly classified control cases to total number of control cases. A short tree size defining a low cost value signifies better classification of the two data groups. This also signifies a higher sensitivity and specificity of the peaks to describe the ability of the classification trees to differentiate the ALS and control groups. The final tree size is determined using a cross validation method, in which the tree is built on a fraction of the data and then the remainder of the data is utilized to assess the tree error rate. This tree building process determines the spectra most valuable in terms of delineating the two sets of data (i.e., ALS vs. control).

The Rules Learning (RL) parameters algorithm was first used to learn rules for predicting mass spectra of complex organic molecules (see, e.g., Feigenbaum et al., *Artificial Intelligence*, 59, 233-240 (1993)) and views inductive learning as a knowledge-based problem solving activity that can be implemented in the heuristic search paradigm. RL primarily searches possible rules by successive specialization, guided by data in the training set and by prior knowledge about the data (e.g., clinical diagnosis or symptoms, subject medications) to define diagnostic biomarkers.

RL has been applied to numerous scientific, commercial, and medical data sets (see, e.g., Lee et al., *Environ Health Perspect.*, 104 *Suppl* 5, 1059-63 (1996)). The main method adopted by RL is hypothesis testing through generation of hypotheses and testing by evidence gathering. Several different kinds of statistics are employed during evidence gathering. These include an estimation of certainty factor (cf) for each rule, together with its positive predictive value and p-value. The RL program will generate predictive rules from two-thirds of the samples within the dataset, re-iterate this rule generation phase three times to develop the best rule set, and then apply these rules to the remaining one-third of the samples to test the ability of the rules to make proper predictions.

Example 1

This example demonstrates the identification of the mass spectral profile of proteins in cerebrospinal fluid (CSF) isolated from ALS patients.

The Ciphergen Bio Wizard Software version 3.1 was used to perform a univariate analysis of both the SAX2 and Zn-IMAC3 datasets to identify CSF spectral peaks that exhibit statistically significant peak intensities between the control and ALS subjects. A total of 366 peaks (207 on SAX2 chip and 159 on Zn-IMAC3 chip) were observed in the CSF samples and subsequently examined by the data analysis described above. As shown in Table 1, 51 protein peaks were identified from the SAX2 dataset that exhibited a statistically significant difference in peak intensity between control and ALS subjects (either increased or decreased expression levels). Many of these spectral peaks exhibited extremely significant p values ($p<0.001$). 43 spectral peaks also were identified from the Zn-IMAC3 dataset that exhibited a statistically significant difference in expression levels between the control and ALS subjects (Table 2). In total, 94 protein peaks (25%) exhibited significant alterations in peak intensity between the control and ALS subjects.

TABLE 1

Differential protein levels in SAX2 dataset

| m/z (Da) | p-value | ALS | | Control | |
|---|---|---|---|---|---|
| | | Mean | Standard Deviation | Mean | Standard Deviation |
| 2146.838 | 1.8E−05 | 2.1024105 | 1.044183 | 0.436675767 | 0.618506 |
| 6259.543 | 2.8E−05 | 0.28171616 | 0.352692 | 0.91939133 | 0.323649 |
| 6979.098 | 0.00027 | 0.6138643 | 0.590915 | 1.683851264 | 0.822486 |
| 13370.43 | 0.00027 | 0.47592359 | 0.71069 | 1.305152796 | 0.657308 |
| 13972.86 | 0.00031 | 0.7326836 | 0.913312 | 1.983968434 | 0.920973 |
| 13914.31 | 0.00056 | 0.98664206 | 0.950395 | 2.238866793 | 1.086189 |
| 6686.678 | 0.00063 | 0.40630932 | 0.485955 | 1.051362062 | 0.527582 |
| 5868.664 | 0.00063 | 0.41583229 | 0.344694 | 1.069356479 | 0.638447 |
| 14088.3 | 0.00101 | 0.55363594 | 0.692485 | 1.270190729 | 0.575205 |
| 15511.17 | 0.00101 | 0.16389265 | 0.131792 | 0.032583059 | 0.04235 |
| 6878.972 | 0.00141 | 0.53067276 | 0.38746 | 1.113267255 | 0.555324 |
| 7260.443 | 0.00157 | 0.41853901 | 0.467867 | 0.956959807 | 0.397975 |
| 4157.481 | 0.00157 | 0.71988459 | 1.098499 | 1.968301916 | 1.322399 |
| 6626.246 | 0.00157 | 0.27504716 | 0.235366 | 0.563100348 | 0.24453 |
| 2395.944 | 0.00196 | 1.34648023 | 0.67716 | 0.727358652 | 0.76988 |
| 7046.957 | 0.00218 | 0.40670077 | 0.421447 | 0.861796267 | 0.36926 |
| 3269.22 | 0.00243 | 0.44635633 | 0.282654 | 0.188886521 | 0.235535 |
| 13874.69 | 0.0027 | 1.1596816 | 1.112424 | 2.142619336 | 1.078312 |
| 3909.932 | 0.003 | 1.16813719 | 1.877956 | 2.420309133 | 1.518664 |
| 10400.41 | 0.00452 | 0.16914618 | 0.065906 | 0.108196224 | 0.044984 |
| 4469.995 | 0.00551 | 0.54129192 | 0.509075 | 1.028762513 | 0.483909 |
| 11478.86 | 0.00551 | 0.66155951 | 0.570872 | 0.069061071 | 0.074134 |
| 4810.469 | 0.00608 | 0.60063531 | 0.601494 | 1.263977742 | 0.624722 |
| 6931.823 | 0.00608 | 0.65730151 | 0.645726 | 1.123880485 | 0.599914 |
| 2069.124 | 0.0067 | 3.59412333 | 2.817659 | 1.840077386 | 2.536099 |
| 13768.58 | 0.0067 | 4.7000085 | 1.40938 | 6.447086884 | 1.977628 |
| 3514.373 | 0.00738 | 0.74678934 | 1.038997 | 1.798215946 | 1.611327 |
| 5069.708 | 0.00892 | 0.32980277 | 0.299013 | 0.690651136 | 0.509238 |
| 2233.065 | 0.00979 | 1.68433476 | 0.77301 | 1.052755802 | 0.861263 |
| 2292.794 | 0.00979 | 3.66401737 | 2.66177 | 1.962723438 | 2.619796 |
| 2497.948 | 0.00979 | 4.93686389 | 3.699872 | 2.536117714 | 3.311748 |
| 14793.82 | 0.00979 | 0.26973156 | 0.227573 | 0.053444593 | 0.057642 |
| 8185.127 | 0.01074 | 0.24426081 | 0.261578 | 0.425468285 | 0.202575 |
| 11955.94 | 0.01074 | 0.26395957 | 0.279045 | 0.536746605 | 0.298616 |
| 4353.455 | 0.0141 | 0.79353931 | 0.880272 | 1.365675977 | 0.792896 |
| 3923.33 | 0.0141 | 0.54222898 | 0.761263 | 0.94545149 | 0.553145 |
| 2721.833 | 0.01541 | 2.53238563 | 1.92618 | 1.267521436 | 1.672441 |
| 2191.551 | 0.01541 | 1.14190349 | 0.743851 | 0.541847011 | 0.646725 |
| 13064.23 | 0.02 | 0.53854564 | 0.547027 | 0.091196873 | 0.046966 |

TABLE 2

Differential protein levels in Zn-IMAC3 dataset

| m/z (Da) | p-value | ALS | | Control | |
|---|---|---|---|---|---|
| | | Mean | Standard Deviation | Mean | Standard Deviation |
| 2606.872 | 3E−06 | 1.46614051 | 1.08538 | 0.164131169 | 0.149778 |
| 3361.437 | 5.7E−05 | 0.85391165 | 0.413139 | 0.322697433 | 0.326189 |
| 15165.69 | 7.4E−05 | 0.30897956 | 0.212692 | 0.087115582 | 0.168012 |
| 13778.72 | 8.5E−05 | 2.6394018 | 1.199919 | 5.352371029 | 1.787797 |
| 10391.08 | 8.5E−05 | 0.23092941 | 0.075413 | 0.139187337 | 0.043368 |
| 3287.339 | 0.00013 | 0.59232279 | 0.339466 | 0.172128378 | 0.173015 |
| 2075.452 | 0.00027 | 1.34843941 | 0.913213 | 0.239626696 | 0.266465 |
| 6860.747 | 0.00035 | 1.48475126 | 0.88264 | 3.666845489 | 1.765021 |
| 12866.93 | 0.00035 | 0.08765615 | 0.064965 | 0.188936888 | 0.097358 |
| 15354.25 | 0.00056 | 0.10719261 | 0.069777 | 0.037838087 | 0.060333 |
| 7889.502 | 0.00063 | 0.46166968 | 0.109442 | 0.303328123 | 0.163148 |
| 13112.19 | 0.00063 | 0.10242277 | 0.078777 | 0.227452495 | 0.093048 |
| 2117.536 | 0.00126 | 0.97437515 | 0.726592 | 0.33699567 | 0.269119 |
| 13377.4 | 0.00141 | 1.59262519 | 0.892223 | 3.30999521 | 1.58153 |
| 3406.02 | 0.00218 | 0.32736732 | 0.323982 | 0.164240638 | 0.126667 |
| 6895.486 | 0.0027 | 0.51954083 | 0.252104 | 0.915170677 | 0.3946 |
| 5332.608 | 0.00369 | 0.40748307 | 0.226509 | 0.195831387 | 0.310382 |
| 3614.27 | 0.00408 | 0.6093364 | 0.327072 | 0.285075051 | 0.286153 |
| 3856.098 | 0.00452 | 0.84632716 | 0.648593 | 0.361402403 | 0.32473 |
| 6477.169 | 0.00499 | 0.53045071 | 0.227296 | 0.308457976 | 0.175521 |
| 11745.41 | 0.00551 | 2.41192811 | 1.492978 | 4.121649653 | 1.788273 |
| 14072.32 | 0.00551 | 1.59432286 | 0.891964 | 2.56959658 | 1.038702 |

TABLE 2-continued

Differential protein levels in Zn-IMAC3 dataset

| | | ALS | | Control | |
|---|---|---|---|---|---|
| m/z (Da) | p-value | Mean | Standard Deviation | Mean | Standard Deviation |
| 13587.3 | 0.00608 | 0.26678336 | 0.129853 | 0.549015446 | 0.324257 |
| 13958.63 | 0.00608 | 2.87923519 | 1.595817 | 4.451430689 | 1.592695 |
| 11954.81 | 0.0067 | 0.58159052 | 0.317956 | 0.997857242 | 0.428859 |
| 4094.157 | 0.00738 | 1.28933491 | 0.958702 | 0.584966195 | 0.597208 |
| 7654.609 | 0.00892 | 0.9999895 | 0.495137 | 0.663557869 | 0.380283 |
| 12565.62 | 0.01289 | 0.05958173 | 0.047553 | 0.151399506 | 0.16233 |
| 13899.92 | 0.01541 | 3.2112109 | 1.69805 | 4.772234359 | 1.633409 |
| 3439.069 | 0.01682 | 0.99903188 | 0.814756 | 0.39602452 | 0.419786 |
| 4536.418 | 0.01835 | 0.63514335 | 0.53736 | 0.280699358 | 0.317566 |
| 4296.498 | 0.02574 | 0.79721374 | 0.682301 | 0.331189514 | 0.275986 |
| 6964.485 | 0.02574 | 1.79907977 | 0.661589 | 2.355455195 | 0.715553 |
| 7737.347 | 0.03286 | 0.57870448 | 0.296983 | 0.394222148 | 0.217884 |
| 14593.96 | 0.03286 | 0.07007311 | 0.04385 | 0.166535054 | 0.161511 |
| 5624.069 | 0.03558 | 0.37216165 | 0.185979 | 0.229110611 | 0.160466 |
| 6015.861 | 0.03558 | 0.36144362 | 0.202519 | 0.232510716 | 0.17274 |
| 4417.264 | 0.03849 | 0.52366208 | 0.460362 | 0.247342935 | 0.231494 |
| 9954.18 | 0.04159 | 0.23872089 | 0.107352 | 0.180504223 | 0.069646 |

This example demonstrates the mass spectral profile of a sample isolated from a human ALS patient as compared to the mass spectral profile of a sample isolated from a human who does not suffer from ALS.

Example 2

This example demonstrates the identification of a biomarker pattern for the diagnosis of ALS.

As described above, two different computer assisted algorithms were used to identify potential diagnostic biomarkers from the proteomic signatures of CSF from control and ALS subjects. The first algorithm was the Ciphergen Biomarker Patterns Software (BPS) package version 3.1. BPS creates classification trees containing one or more protein peaks that are used to predict disease status. An example of such a classification tree for the SAX2 dataset is shown in FIG. 1. The first peak used was at 6254 Da. The 11 patients with a peak value less than the cut-off are in the left node, of which 100% are ALS patients. The right node contains 23 subjects that were further split at a 6881 Da peak. Three subjects in the left node all were controls. The 20 subjects were then split at the 9939 Da peak, with 1 subject in the left node and 19 subjects in the right node. This classification tree could predict ALS during the learning phase with 100% sensitivity and specificity. The BPS software then randomizes the dataset and uses the classification tree to make predictions that can be compared to the known diagnosis during the test phase. The SAX2 classification tree could then predict ALS subjects with a sensitivity of 74% and a specificity of 95%.

Figure 2:
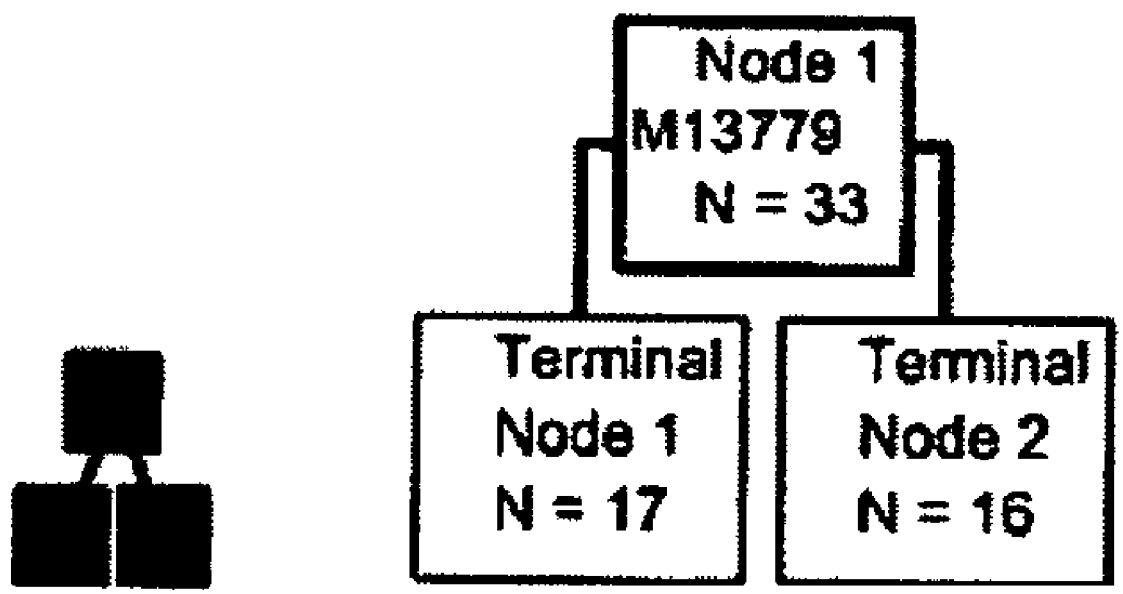
FIG. 2 is a diagram depicting a classification tree generated by Ciphergen Biomarker Patterns Software for the diagnosis of ALS using a Zn-IMAC3 ProteinChip®.

BPS also was used to identify potential biomarkers from the Zn-IMAC3 ProteinChip dataset (FIG. 2). In this classification tree, a single protein peak of 13779 Da was used to predict ALS with 100% sensitivity and 89% specificity during the learning phase. This same classification tree could predict ALS during the cross-validation test phase with 87% sensitivity and 89% specificity.

The second analysis tool used to identify potential biomarkers from CSF was the Rules Learning (RL) program. This program creates a series of learned rules that can predict disease status of subjects. The rules are generated during a learning phase using two-thirds of the dataset subjects. A three-fold validation of the generated rules is performed to generate the final rules set. The remaining dataset subjects (one-third of the total) are retained in a separate bin, randomized, and then the rules applied to predict disease status in this testing phase. The predictions are then compared to the known clinical diagnosis for each subject to determine the sensitivity and specificity of the RL generated rules. For the SAX2 dataset, RL identified 9 rules using 7 protein peaks. For each rule, the absolute values of the protein peak spectral intensities were provided that represent each predictive diagnostic measure. For example, the sample was a control subject if the spectra intensity value (x) for the 6828 Da protein peak was greater than or equal to 0.103 and less than 0.856. These rules accurately predicted the ALS disease status with 100% sensitivity and 81% specificity in the test dataset. The RL program was also applied to the Zn-IMAC3 dataset. This ProteinChip recognizes zinc-binding proteins within the CSF. The RL program generated 7 rules using 6 protein peaks of 6546, 6860, 7530, 13380, 15160, and 15870 Da. These rules predicted the ALS disease status with 100% accuracy and 90% specificity in the test dataset.

The results generated by the BPS and RL analytical tools were compared and a series of protein peaks commonly used to create predictions of subject diagnosis were uncovered. The common predictive biomarkers included proteins of 6250, 5860, 13779, 13958, and 15160 Da. Two of these proteins (13779 and 15160 Da) were identified from the Zn-IMAC3 chip and likely represent zinc-binding proteins that exhibit differential expression in ALS patients. These five protein peaks represent biomarkers with the most predictive value as demonstrated by identification by two distinct algorithms. BPS also identified four unique protein peaks from the SAX2 and Zn-IMAC3 chips as diagnostic indicators and the RL program identified an additional 8 protein peaks as diagnostic indicators. Therefore a total of 17 protein peaks from two ProteinChips and two algorithms were identified as diagnostic indicators for ALS. A total of nine subject misclassifications were found using BPS, and no misclassifications were found using the RL program.

Example 3

This example demonstrates the identification of a protein biomarker present in the mass spectral profile of sample obtained from a human suffering from ALS.

CSF was collected from an ALS patient via lumbar puncturing as described above. To enrich the sample for biomarker identification, 500 µl of the CSF sample was fractionated by anion exchange fractionation using a Q HyperD column (Ciphergen Biosystems, Inc., Fremont, Calif.). Fractions were separated via stepwise elution and were collected at pH9, pH7, pH5, pH4, and pH3. Each fraction was analyzed by mass spectroscopy as described above to identify biomarker peaks of interest. Three biomarker peaks were identified in the pH4 fraction: a 6.2 kDa peak, a 13.3 kDa peak, and a 13.7 kDa peak. This fraction was concentrated using a YM-30 Microcon centrifugal filter (Millipore Corp, Billerica, Mass.). The flow-through was dried using a SpeedVac, resuspended in SDS-PAGE sample buffer (Invitrogen, Carlsbad, Calif.), and resolved on a 12% Bis-Tris gel.

Following silver staining of the gel, four bands were excised and purified from the pH4 fraction, which corresponded to the 13.3 kDa and 13.7 kDa protein peaks. Specifically, three gel plugs were excised from each band using a Pasteur pipette. Gel pieces were washed with 200 µl 50% MeOH/10% acetic acid for 30 minutes at room temperature. The gel pieces were then dehydrated with 100 µl acetonitrile (ACN) for 15 minutes at room temperature.

Proteins were extracted from the gel pieces with 70 µl 50% formic acid/25% ACN/15% isopropanol/10% water for two hours at room temperature with vigorous shaking. 2 µl of the extract were applied to an NP20 ProteinChip Array (Ciphergen Biosystems, Inc., Fremont, Calif.) and allowed to dry. 1 µl of the energy absorbing molecule sinapinic acid (SPA) was added to each protein spot twice. Arrays were analyzed on a PBSIIc mass spectrometer protein chip reader (Ciphergen Biosystems, Inc., Fremont, Calif.).

The resulting mass spectroscopic "fingerprints" of the 13.3 kDa and 13.7 kDa peaks were compared to known protein sequences with peptide mass information in the ProFound database (Version 4.10.5, The Rockefeller University). Based on these comparisons, cystatin C and transthyretin were identified as candidate proteins corresponding to the 13.3 kDa protein peak and the 13.7 kDa protein peak, respectively.

This example demonstrates the identification of the proteins corresponding to the 13.3. kDa and 13.7 kDa biomarkers present in a sample isolated from a human suffering from ALS.

Example 4

This example demonstrates the identification of subsets of protein biomarkers that can be used to diagnose ALS in a patient.

Using the RL algorithm for the SAX2 dataset and the Zn-IMAC3 as described above, subsets of biomarkers that can be used to diagnose ALS were identified. One such subset contained 10 biomarkers that diagnose ALS with 92% sensitivity and 86% accuracy from blinded test subjects (see Table 3). These biomarkers were most predictive for "early" stage disease. That is, this panel was not predictive for ALS patients greater than 1100 days after time of symptom onset.

A second subset contained 7 biomarkers that diagnose ALS with 100% accuracy (see Table 4), while a third subset also contained 7 biomarkers that diagnose ALS with 100% accuracy (see Table 5).

TABLE 3

| Rule | Diagnosis |
|---|---|
| SAX2 3.707 in −0.113 ≦ x < 0.078 | Negative |
| Zn 13.395 in 0.079 ≦ x < 0.137 | Negative |
| Zn 8.931 in 0.170 ≦ x < 0.289 | Negative |
| Zn 16.595 in 0.048 ≦ x < 0.072 | Negative |
| Zn 3.052 in 0.24 ≦ x < 0.516 | Negative |
| SAX2 7.775 in 4-High | ALS |
| Zn 17.087 in 2-Low | ALS |
| SAX2 11.524 in 2-Low | ALS |
| Zn 8.616 in 2-Low | ALS |
| Zn 9.098 in 2-Low | ALS |

TABLE 4

| Rule | Diagnosis |
|---|---|
| SAX2 13647.294 in 0.185 ≦ x < 0.335 | Negative |
| SAX2 6878.7475 in 0.095 ≦ x < 0.103 | ALS |
| Zn 3010.6341 in 0.302 ≦ x < 0.481 | ALS |
| Zn 8931.1149 in 0.274 ≦ x < 0.482 | Negative |
| SAX2 2404.9228 in 0.335 ≦ x < 0.516 | Negative |
| SAX2 2459.2504 in 0.731 ≦ x < 1.018 | ALS |
| SAX2 7771.1084 in 4-High | ALS |

TABLE 5

| Rule | Diagnosis |
|---|---|
| SAX2 2404.9228 in 0.335 ≦ x < 0.516 | Negative |
| Zn 13098.084 in 0.341 ≦ x < 0.537 | Negative |
| SAX2 6863.9447 in 0.308 ≦ x < 0.543 | Negative |
| Zn 8931.1149 in 0.274 ≦ x < 0.482 | Negative |
| SAX2 4750.9489 in 0.390 ≦ x < 0.615 | ALS |
| Zn 3010.6341 in 0.302 ≦ x < 0.481 | ALS |
| Zn 7742.4264 in 2-Low | ALS |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for diagnosing amyotrophic lateral sclerosis (ALS) in a human subject, which method comprises: (a) determining a mass spectral profile of proteins in a cerebrospinal fluid sample obtained from the subject: and (b) diagnosing the subject with ALS when the mass spectral profile of the sample comprises an increase in intensity of a 3.42 kDa peak corresponding to the C-terminal fragment of human 7B2 protein relative to a control, a decrease in intensity of a 13.3 kDa peak corresponding to human cystatin C protein relative to a control, and a decrease in intensity of a 13.7 kDa peak corresponding to human transthyretin protein relative to a control.

2. The method of claim 1, wherein the control is the mass spectral profile of a sample obtained from a subject that does not suffer from ALS.

3. A method for selecting a drug for treating amyotrophic lateral sclerosis (ALS) in a subject by assessing the effectiveness of a drug in treating ALS in a human subject, which method comprises:
  (a) determining a mass spectral profile of proteins in a first cerebral spinal fluid sample obtained from the subject, wherein the mass spectral profile of the first sample comprises a 3.42 kDa peak corresponding to the C-terminal fragment of human 7B2 protein, a 13.3 kDa peak corresponding to human cystatin C protein, and/or a 13.7 kDa peak corresponding to human transthyretin;
  (b) administering a drug to the subject,
  (c) determining a mass spectral profile of proteins in a second cerebral spinal fluid sample obtained from the subject after administration of the drug in step (b),
  (d) comparing the mass spectral profile of the first sample to the mass spectral profile of the second sample and
  (e) selecting the drug for treating ALS that induces a change in the average protein peak intensity values of the mass spectral profile of the second sample as compared to the average protein peak intensity values of the mass spectral profile of the first sample for the 3.42 kDa peak corresponding to the C-terminal fragment of human 7B2 protein, the 13.3 kDa peak corresponding to human cystatin C protein, and the 13.7 kDa peak corresponding to transthyretin.

* * * * *